(12) United States Patent
Kaiser et al.

(10) Patent No.: US 7,272,432 B2
(45) Date of Patent: Sep. 18, 2007

(54) METHOD AND APPARATUS FOR ANALYZING A PHYSIOLOGICAL WAVEFORM

(75) Inventors: Willi Kaiser, Emmendingen (DE); Martin Findeis, Freiburg (DE)

(73) Assignee: GE Medical Systems Information Technology GmbH (DE)

( * ) Notice: Subject to any disclaimer, the term of this patent is extended or adjusted under 35 U.S.C. 154(b) by 382 days.

(21) Appl. No.: 10/757,174

(22) Filed: Jan. 14, 2004

(65) Prior Publication Data
US 2004/0147849 A1    Jul. 29, 2004

Related U.S. Application Data

(62) Division of application No. 09/578,297, filed on May 25, 2000, now Pat. No. 6,701,182.

(51) Int. Cl.
*A61B 5/04* (2006.01)
(52) U.S. Cl. ................................... 600/509
(58) Field of Classification Search ............. 600/382, 600/384, 509, 522, 523, 525; 128/903
See application file for complete search history.

(56) References Cited

U.S. PATENT DOCUMENTS

| | | | |
|---|---|---|---|
| 4,987,901 A | 1/1991 | Kunig | |
| 5,687,735 A | 11/1997 | Forbes et al. | |
| 5,876,351 A * | 3/1999 | Rohde | 600/523 |
| 5,967,994 A * | 10/1999 | Wang | 600/509 |
| 6,119,035 A * | 9/2000 | Wang | 600/509 |
| 6,238,338 B1 * | 5/2001 | DeLuca et al. | 600/300 |
| 6,263,235 B1 | 7/2001 | Kaiser et al. | |
| 6,266,554 B1 | 7/2001 | Hsu et al. | |

OTHER PUBLICATIONS

Kaiser, Wili et al. "Artifact Processing During Exercise Testing," Journal of Electrocardiology, vol. 32, Supplement 1999, pp. 212-219.
Van Alste, et al. "Removal of Base-Line Wander and Power-Line Interference form the ECG by an Efficient FIR Filter with Reduced Number of Taps," IEEE Transactions on Biomedical Engineering, vol. BME-32, No. 12, Dec. 1995.

* cited by examiner

*Primary Examiner*—Carl Layno
*Assistant Examiner*—Frances P. Oropeza
(74) *Attorney, Agent, or Firm*—Andrus, Sceales, Starke & Sawall, LLP

(57) ABSTRACT

A method and apparatus for analyzing a physiological waveform. The apparatus comprising an input terminal for connection to a patient to acquire the physiological waveform from a patient, an instrumentation amplifier connected to the input terminal to filter the physiological waveform, and an analysis module including a processor and software for operating the processor to detect cyclic artifact in the physiological waveform. The method comprising the acts of obtaining the physiological waveform and determining whether there is more than one independent complex rhythm within the digital physiological waveform.

22 Claims, 6 Drawing Sheets

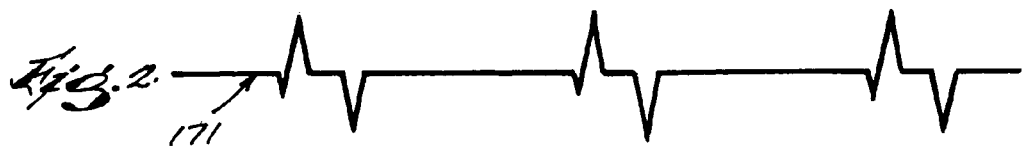
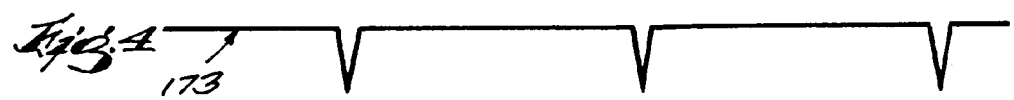
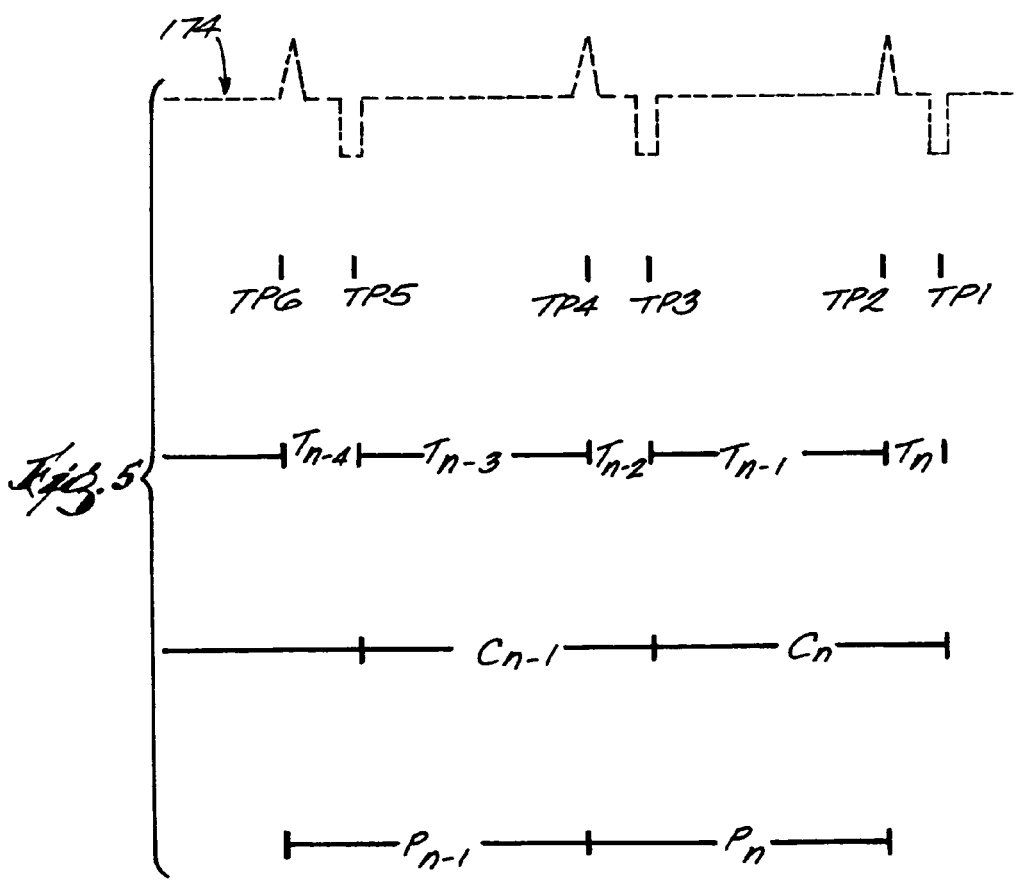

METHOD AND APPARATUS FOR ANALYZING A PHYSIOLOGICAL WAVEFORM

CROSS REFERENCE TO RELATED APPLICATIONS

This patent application is a divisional application of U.S. application Ser. No. 09/578,297, filed on May 25, 2000.

BACKGROUND OF THE INVENTION

The invention relates to an apparatus for analyzing a physiological waveform, and particularly to a medical device for acquiring, analyzing and selecting a multi-lead electrocardiogram.

Electronic medical devices are used to acquire, record and manipulate a variety of different data with the purpose of analyzing a patient's health. An electrocardiogram (ECG) is one example of data that is acquired, recorded and manipulated using an electronic medical device. The ECG is a valuable record of the electrical impulses stimulating a patient's heart and is used to analyze the patient's health. An example where an ECG is important is when a patient performs an exercise test. The ECG can be used to, among other things, calculate a patient's heart rate or determine if the patient has an arrhythmia.

SUMMARY OF THE INVENTION

During an exercise test, one or more patient monitors are connected to a patient to record physiological information generated by the patient. One particularly important measurement obtained is an ECG, i.e., a representation of the electrical impulses generated by the patient's heart. A plurality of electrodes (e.g., 10 electrodes) are placed on the patient (e.g., in a standard 12-lead electrode placement) to acquire a multi-lead ECG signal from the patient. However, because the patient is exercising (i.e., moving), the patient's muscles constrict and contract and create noise potential (commonly called muscle artifact) which is acquired by the electrodes. Additionally, because the patient moves, the electrodes also move resulting in an impedance change in the patient-electrode connection. The impedance change of the electrodes results in an additional artifact signal in the ECG. Because the movement is typically a repetitive movement (e.g., running at a constant speed on a treadmill), the artifact generated thereby is typically a cyclic artifact over the short-term.

The resulting cyclic artifact is similar to the frequency content associated with the cardiac cycle. This results in the cyclic artifact being difficult to detect and difficult to remove from the ECG. Moreover, the artifacts are dangerous to cardiac cycle analysis because the artifact disturb the detection of QRS complexes. Disturbing detection of QRS complexes may lead to improper heart rate detection, erroneous arrhythmia analysis results, and a poor assessment of cardiovascular health.

Because the electrodes for acquiring the ECG signals are placed in different locations on the patient, different ECG leads will register different levels of the cyclic artifact. However, for QRS complex detection, heart rate calculation and arrhythmia analysis, it is not necessary to use all leads. A monitor can take advantage of the redundancy found in multi-lead systems and select only leads with good ECG quality. By selecting only good leads during exercise testing, the QRS complex detection quality can be improved.

Accordingly, the invention provides a medical device for acquiring and analyzing a physiological waveform. The medical device includes an input terminal for connection of a plurality of electrodes to a patient to acquire the physiological waveform from the patient, an instrumentation amplifier connected to the input terminal to filter the physiological waveform, and an analysis module including a processor and software for operating the processor to detect artifact in the physiological waveform.

The invention further provides a medical device for acquiring and analyzing a physiological signal. The medical device includes an input terminal for connection to a patient to acquire a physiological signal from the patient, an instrumentation amplifier connected to the input terminal to filter and amplify the physiological signal, and means for detecting cyclic artifacts in the physiological signal.

The invention further provides a medical device for acquiring and analyzing a multi-lead electrocardiogram. The medical device includes an input terminal for connection to a patient to acquire multi-lead ECG signals from the patient, an instrumentation amplifier connected to the input terminal to filter the ECG signals and combine the signals to generate a multi-lead ECG, and an analysis module including a processor and software for operating the processor to detect cyclic artifact in the multi-lead ECG and select a led for analysis based on a lack of cyclic artifact in that lead.

The invention further provides a method of analyzing a lead of a multi-lead electrocardiogram (ECG), where each lead has one or more independent complex rhythms. The method includes the acts of obtaining the ECG and determining whether there is more than one independent complex rhythm within the lead. The method further includes selecting the first lead for analysis if there is only one independent complex rhythm within the first lead. The method further includes the acts of determining whether there is more than one independent complex rhythm within the second lead and selecting the lead for analysis if there is only one independent complex rhythm within the second lead.

The invention further provides a software program for detecting cyclic artifact in a multi-lead electrocardiogram (ECG), where each lead has one or more independent complex rhythms. The software program detects the artifact by sampling the ECG and processing a lead to determine whether there is more than one independent complex rhythm within the lead. In addition, the software program selects the lead for analysis if there is not more than one independent complex rhythm within the lead.

Other features and advantages of the invention will become apparent to those skilled in the art upon review of the following detailed description, claims, and drawings.

BRIEF DESCRIPTION OF THE DRAWINGS

FIG. 2 is a chart displaying an exemplary lead of a multi-lead ECG which includes a cyclic artifact waveform and a cardiac cycle waveform.

FIG. 3 is a chart displaying an exemplary cardiac cycle waveform of a lead.

FIG. 5 is a schematic representation of the lead shown in FIG. 2.

FIG. 7 is a flow-chart of a method implementing the act of determining whether the value (x) is a trigger point.

DETAILED DESCRIPTION

Before one embodiment of the invention is explained in full detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including" and "comprising" and variations thereof herein is meant to encompass the items listed thereafter and equivalents thereof as well as additional items.

Figure 1:
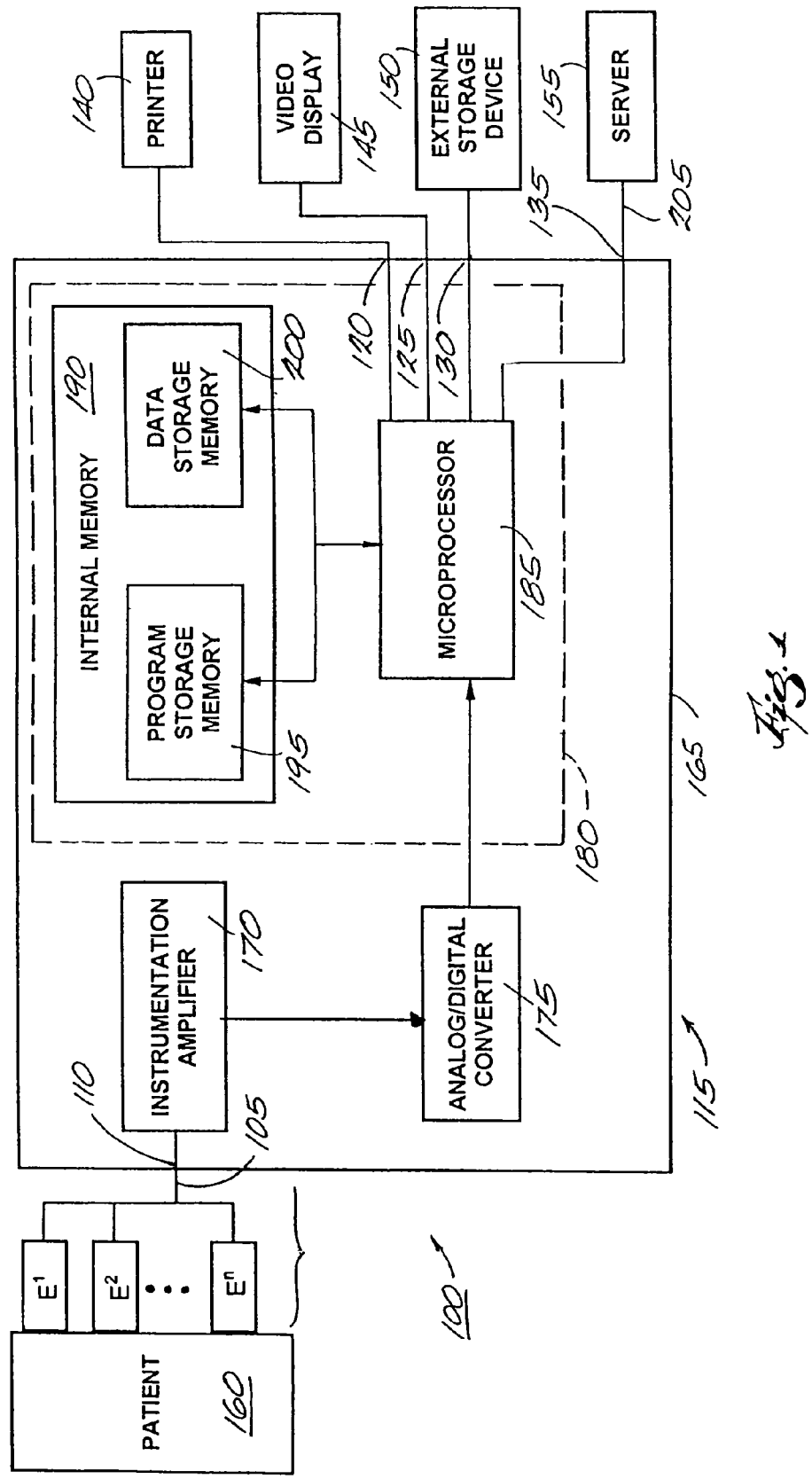
FIG. 1 is a schematic representation of a monitor embodying the invention.
Figure 6:
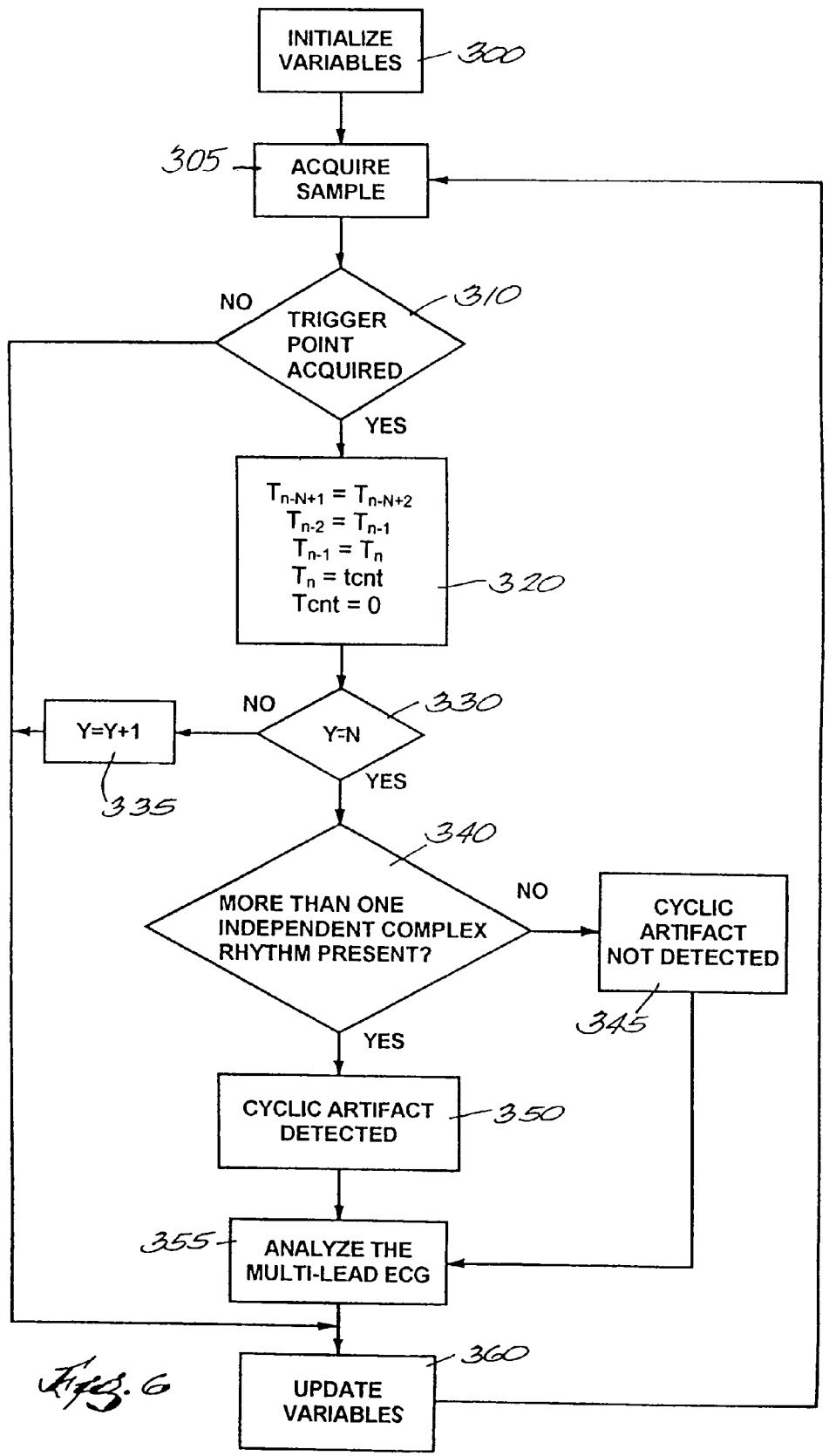
FIG. 6 is a flow-chart of a method embodying the invention.

Shown in FIG. 1 of the drawings is a monitor 100 embodying the invention. In general terms, the monitor 100 includes a plurality of electrodes $E_1, E_2 \ldots E_n$, an interface cable 105, an input terminal 110, a central processing unit 115, output terminals 120, 125, 130 and 135, and output units 140, 145, 150 and 155. The electrodes $E_1, E_2 \ldots E_n$ are connected to a patient 160, typically a person. The electrodes $E_1, E_2 \ldots E_n$, acquire electrical activity (i.e., a multi-lead ECG signal) generated by the patient. The number of electrodes $E_1, E_2 \ldots E_n$ can vary. The electrodes $E_1, E_2 \ldots E_n$ are electrically connected to an interface cable 105.

The interface cable 105 provides direct electrical connection between the electrodes $E_1, E_2 \ldots E_n$ and input terminal 110 of the central processing unit 115. However, in other embodiments (not shown) the interface cable may electrically connect the electrodes to a remote transmitter, which transmits the signals to a receiver that is electrically connected to the central processing unit 115. The interface cable 105 allows for transmission of the acquired multi-lead ECG signal from the patient to the central processing unit 115. The interface cable 105 is preferably a passive cable but, alternatively, the cable may contain active circuitry (not shown) for amplifying and combining ECG lead signals.

The central processing unit 115 has a housing 165. The housing 165 includes input terminal 110 and output terminals 120, 125, 130 and 135. Additional terminals can be added as needed.

Figure 4:
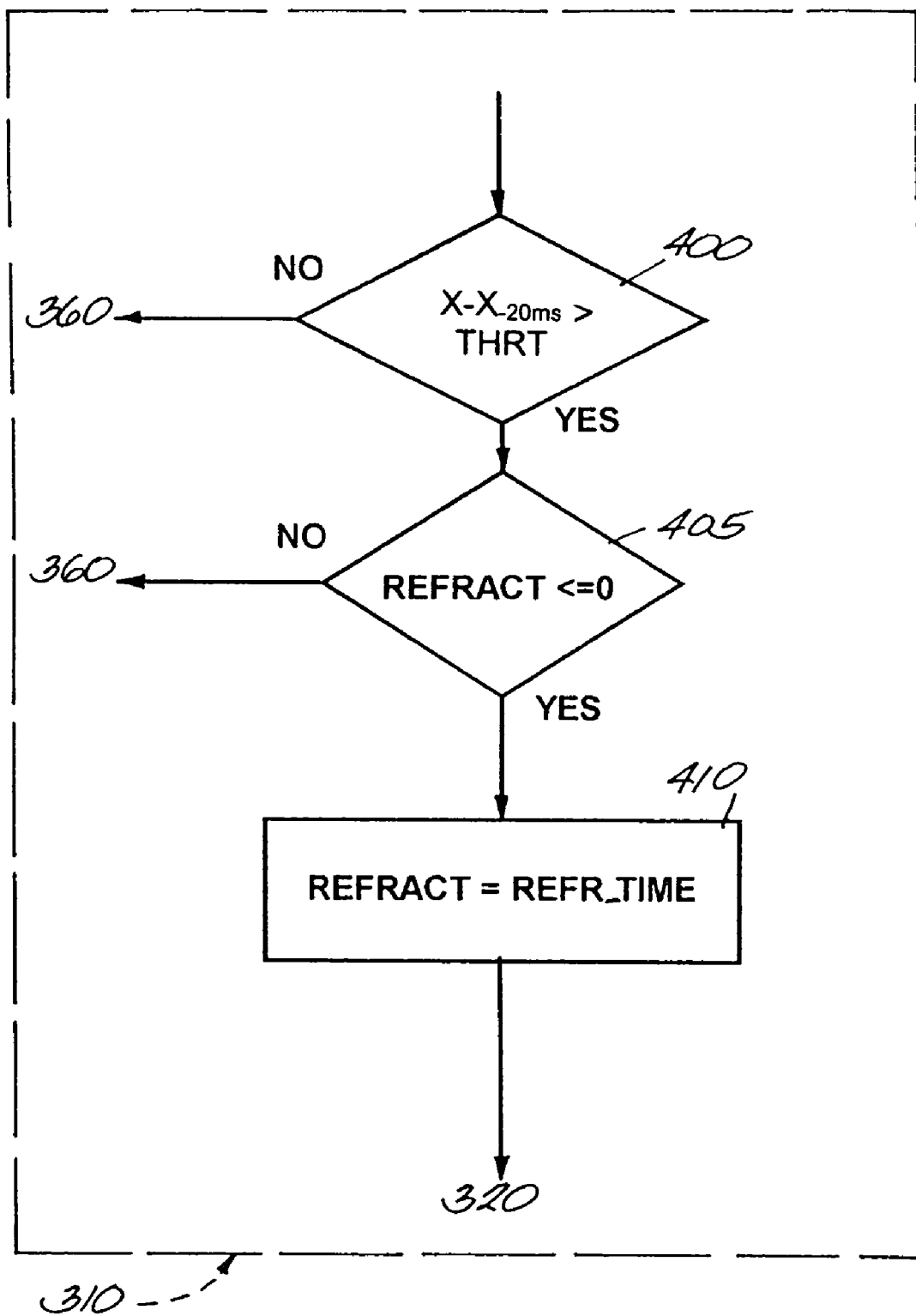
FIG. 4 is a chart displaying an exemplary cyclic artifact waveform.

The central processing unit 115 further includes an instrumentation amplifier 170 connected to the input terminal 110. The instrumentation amplifier receives the multi-lead ECG signal, amplifies the signal, and filters the signal to create an analog multi-lead ECG. The number of leads of the multi-lead ECG can vary without changing the scope of the invention. An example lead of a multi-lead ECG is shown in FIG. 2. The lead 171 includes a cardiac cycle waveform 172 or ECG rhythm (see FIG. 2) and a cyclic artifact waveform 173 or cyclic artifact rhythm (see FIG. 4). A schematic representation 174 of the example lead 171 is shown in FIG. 5.

The central unit 115 further includes an analog-to-digital (A/D) converter 175 electrically connected to the instrumentation amplifier 170. The A/D converter 175 receives the analog multi-lead ECG and converts the analog multi-lead ECG to a digital signal representing the multi-lead ECG.

The central unit 115 further includes a means for detecting cyclic artifact in a physiological waveform. The means for detecting cyclic artifact can be an analysis module 180 that implements a software program (as shown in FIG. 1), an application specific integrated circuit (not shown) or a similar device. The analysis module 180 is electrically connected to the A/D converter 175. The analysis module reads the digital multi-lead ECG at a given sampling rate and determines whether a cyclic artifact rhythm is present within any of the leads of the multi-lead ECG. The analysis module includes a processor 185 and internal memory 190. The internal memory 190 includes program storage memory 195 for storing the software program and data storage memory 200 for storing sampled data.

As shown in FIG. 1, output units 140, 145, 150 and 155 are connected to the central unit 115 at output terminals 120, 125, 130 and 135. The outputs include a printer 140, a video display unit 145, a storage device 150 (e.g., magnetic disk drive, read or write CD ROM, etc.), and a server 155 or other processing unit (e.g., a personal computer). The server 155 is connected via a distributed network 205. Of course, other output units can be attached or the output units (e.g., the video display unit 145) can be incorporated within the central unit 115. Additionally, not all of the output units are required for operation of the monitor 100.

In operation, the monitor 100 of the invention receives electrical activity from the patient 160 in the form of a multi-lead ECG signal, amplifies and filters the received ECG signal to create a multi-lead ECG, and determines if more than one independent complex rhythm is present within any of the leads. The resulting multi-lead ECG and the information regarding whether any lead contains more than one independent complex rhythm is provided to a further portion of the software where the information is used to select leads for analysis. The selection of the leads is disclosed in U.S. patent application Ser. No. 09/421,683, entitled ELECTROCARDIOGRAM ARRANGEMENT, which is incorporated herein by reference. Although the disclosed embodiment analyzes multi-lead ECGs, the monitor of the invention may analyze other physiological waveforms.

Specifically, the electrodes $E_1, E_2 \ldots E_n$ are connected to a patient 160 and acquire electrical activity generated by the patient 160. For example, the system may use ten electrodes that are connected to a patient by a standard twelve-lead placement, and acquire a twelve-lead ECG signal. In an ideal situation, the received electrical activity is generated by the patient's heart (not shown) only. However, in reality, the received electrical activity is from the patient's heart in combination with cyclic and non-cyclic artifact.

After acquiring the patient's electrical activity, the electrodes $E_1, E_2 \ldots E_n$ transmit the electrical activity to the input terminal 110 via the interface cable 105. The electrical activity signals enter the central unit 115 at terminal 110 and are provided to the instrumentation amplifier 170.

The instrumentation amplifier 170 combines, amplifies and filters the electrical activity signals in such a way as to generate a multi-lead ECG to distinguish the multi-lead ECG from other biological signals and noise sources. For example, for the ten electrodes that are placed on a patient using a standard twelve-lead electrode placement, the instrumentation amplifier creates a twelve-lead ECG (i.e., ECGI, ECGII, ECGIII, ECGAVR, ECGAVL, ECGAVF, ECGV1, ECGV2, ECGV3, ECGV4, ECGV5, ECGV6). For other electrode configurations, the number of leads of the multi-lead ECG may vary.

The resulting multi-lead ECG is provided to the A/D converter 175. The A/D converter 175 samples each lead of the multi-lead ECG to create a digital signal representing the multi-lead ECG and provides the digital multi-lead ECG to the analysis module 180. The analysis module 180 acquires the digitally sampled multi-lead signal from the A/D converter 175 and detects whether any cyclic artifact are in each lead of the multi-lead ECG. The analysis module may contain further software for selecting leads for analysis based in part on whether any lead contains cyclic artifact, or may select leads for analysis based only on whether more than one cyclic rhythm is present within any of the leads.

Specifically, the analysis module provides the digital multi-lead ECG to the microprocessor 185. The microprocessor 185 reads or samples the provided digital signal at a sampling rate and applies the sampled multi-lead ECG to a software-created low pass filter to remove unwanted noise. Preferably, the software created low pass filter is a 20 Hz filter. Next, the software determines whether more than one independent, recognizable cyclic rhythm is within each lead. Although there is more than one way to determine if a cyclic artifact is within any of the leads, the exemplary method is disclosed in FIGS. 6, 7, 8 and 9. Since the method is the same for each lead, only one lead will be discussed in detail.

At act 300, the software clears all storage fields and variables, and sets constants to specific values in preparation of implementing the detection of cyclic artifact (DCA) portion of the software. At act 305, a sampled and low-pass filtered voltage value (x) enters the DCA algorithm. The value (x) enters the DCA portion of the software at a rate (Ta).

At act 310, the software determines whether the value (x) is a trigger point ($TP_1$, $TP_2$ . . . ) (See FIG. 5). A trigger point occurs when a complex (i.e., a QRS complex or an artifact complex A) is detected. For the embodiment disclosed, at act 400 (See FIG. 7), the recently obtained value (x) is compared with an old x value (e.g., $x_{-20\ ms}$) to determine if it is greater than a threshold value (THRT) (e.g., 250⊠v). If the difference between the current value (x) and the old value (e.g., $x_{-20\ ms}$) is greater than the threshold value (THRT), then the line created by the two values has a slope sufficiently large to represent the slope of a complex and the software proceeds to act 405. If the difference between the current value (x) and the old value (e.g., $x_{-20\ ms}$) is equal to or less than the threshold value THRT, then the line created by the two values does not have a slope sufficiently large to represent the slope of a complex and the software proceeds to act 360. At act 405, the software determines whether a refractory time (refract) is less than or equal to zero. The refractory time (refract) is a counter that is originally set to a maximum refractory time (REFR_TIME) (e.g., 200 ms) and is reduced each time a value enters the DCA portion of the software (see act 605). If the refractory time (refract) is less than or equal to zero, then a sufficient time period has occurred since the last trigger point has been selected. This guarantees that only one trigger point is selected for the same complex. If the refractory time (refract) is greater than zero, then the software proceeds to act 360. If the refractory time (refract) is less than or equal to zero, then the software proceeds to act 410. At act 410, the refractory time (refract) is reset to the maximum refractory time (REFR_TIME) and the software proceeds to act 320.

When the software proceeds to act 320, the software has determined that a trigger point has been acquired. While the software is acquiring the values (x), a digital timer (tcnt) (See act 605) is counting the time between the current value (x) and the occurrence of the latest trigger point. When the software proceeds to act 320, the software creates a new trigger interval ($T_n$) (see FIG. 5) representing the time difference between the just determined trigger point ($TP_1$) and the previous trigger point ($TP_2$). The current trigger interval ($T_n$) is equal to the digital timer (tcnt).

At act 320, a shift register containing N elements (e.g., ten elements) of previously stored trigger intervals is updated with the new trigger interval. The latest trigger interval is stored in the register at $T_n$ and the earliest trigger interval is stored in the register at $T_{n-(N+1)}$ (see FIG. 6). The shift register updates itself by shifting all the elements back in time (e.g., $T_{n-(N+1)}=T_{n-(N+2)}$ . . . $T_{n-1}=T_n$, $T_n$=tcnt). Additionally, digital timer (tcnt) is reset to 0 (i.e., begins counting to the next trigger point). Thus, a shift register is created which contains the N latest trigger intervals.

At act 330, the software determines whether N trigger intervals (e.g., 10) have been recorded within the shift register. If N intervals have not been recorded, then a counter (Y) is increased at act 335 and the processor precedes to act 360. If N intervals have been recorded, then the software can determine whether there are two independent rhythms present within the lead. By keeping a counter for the number of intervals, the software creates a buffer to more adequately determine whether more than one cyclic rhythm is present within the lead. Once a buffer of N trigger intervals is created, then the software performs real-time calculations. Of course, the number N can vary and is not meant to be a limiting factor.

At act 340, the software determines if the lead contains more than one independent complex rhythm. In general, a current chain of intervals (see FIG. 5) is created, analyzed, and compared with a previously created chain of intervals (see FIG. 5). If only one independent cyclic rhythm is present, the software determines that a cyclic artifact was not detected (act 345). If two independent cyclic rhythms are present, the software determines that a cyclic artifact rhythm is detected (act 350). The software provides the lead to additional software along with the determination of whether a cyclic artifact has been detected for analysis (act 355).

Figure 8:
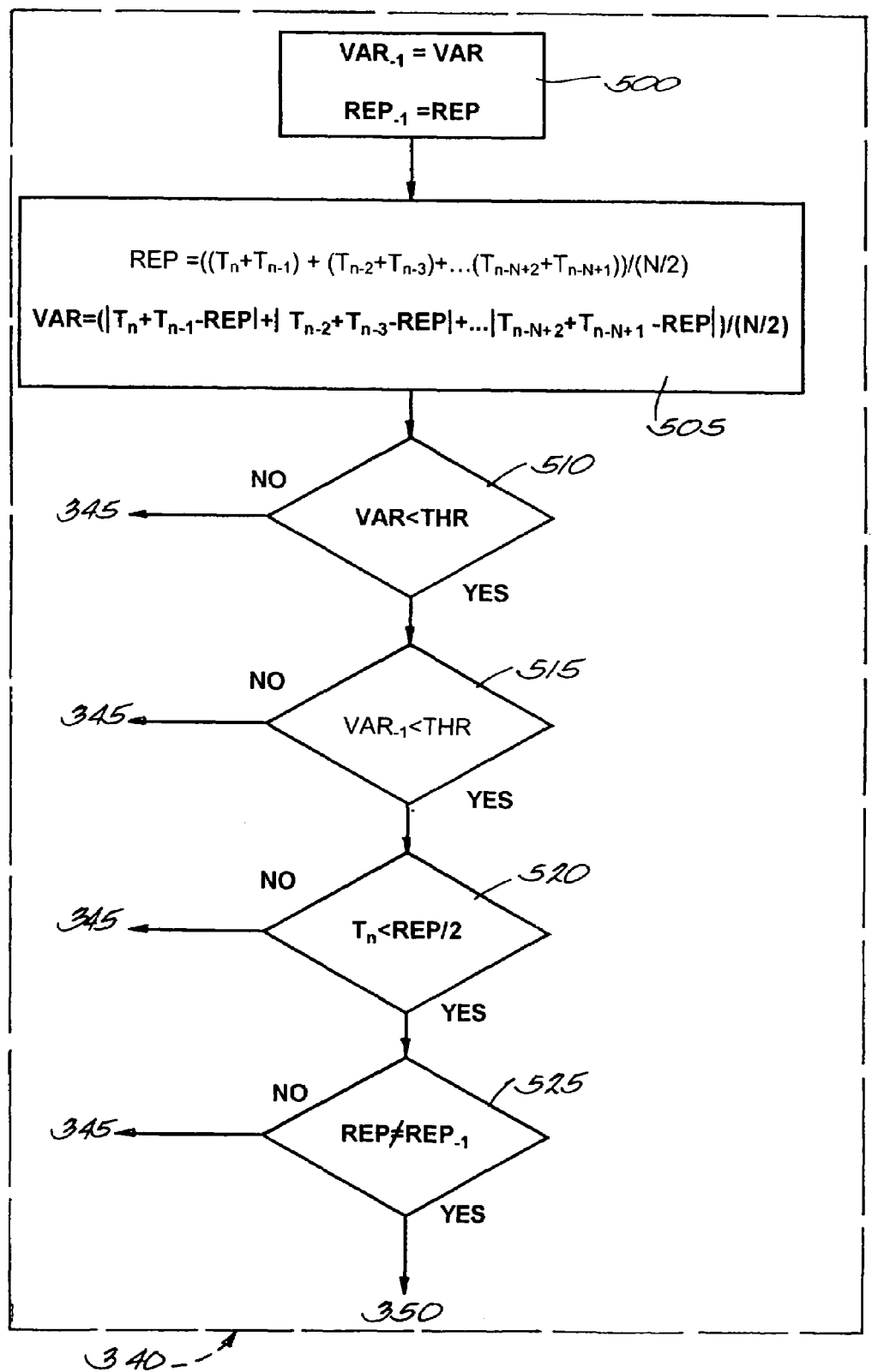
FIG. 8 is a flow-chart of a method implementing the act of determining if the lead contains more than one independent complex rhythm.
Figure 9:
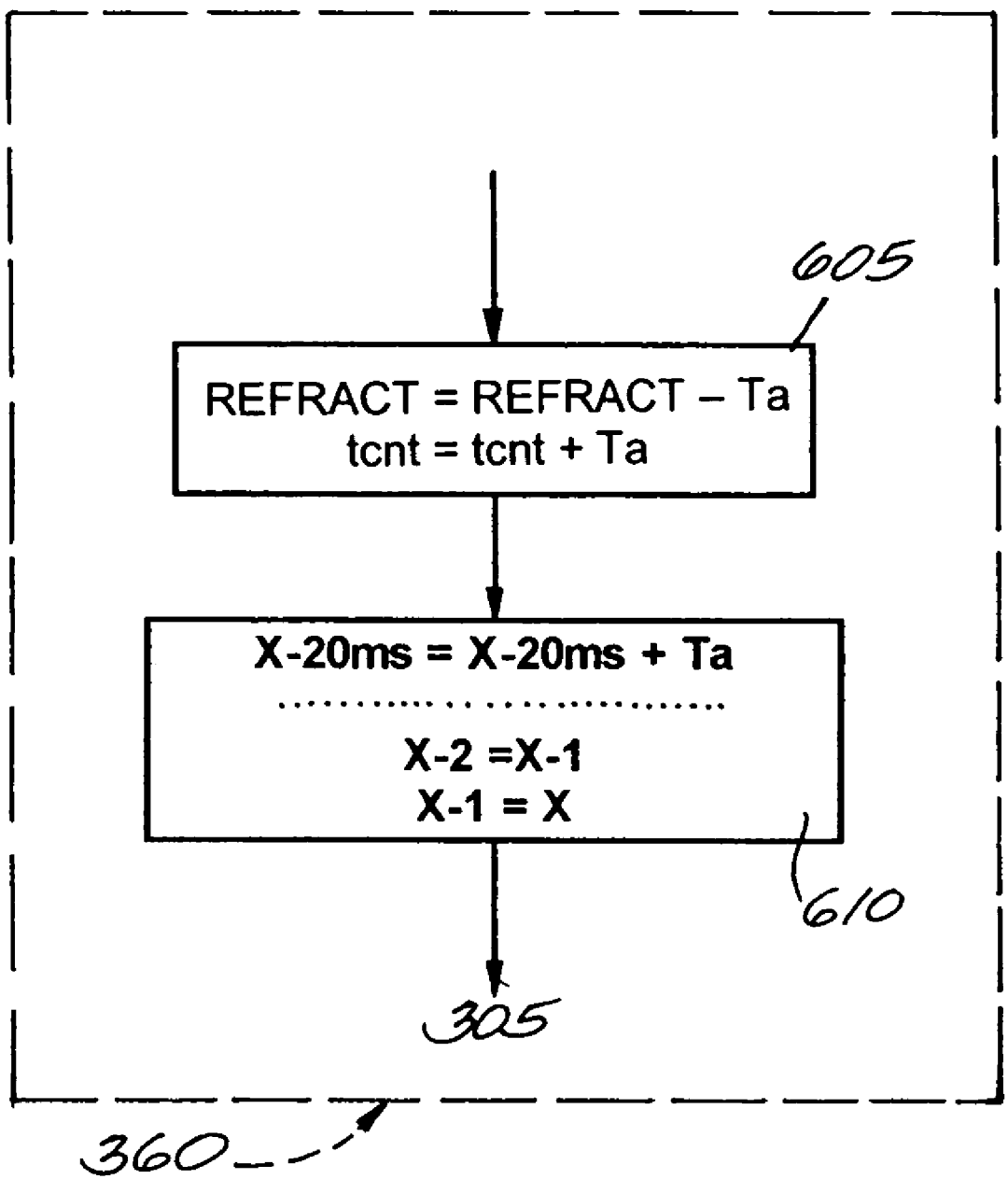
FIG. 9 is a flow-chart of a method implementing the act of updating the program variables.

As shown in act 500 of FIG. 8, a statistical variance of the previous chain is stored in ($var_{-1}$), and a representative or mean interval of the previous chain is stored in ($rep_{-1}$). At act 505, a current representative interval (rep) and a current variance (var) is calculated for the current chain of intervals. The current chain of intervals is represented by the intervals ($T_n+T_{n-1}$), ($T_{n-2}+T_{n-3}$), ($T_{n-4}+T_{n-5}$), . . . (see FIG. 5). The previous chain of intervals is represented by the intervals ($T_{n-1}+T_{n-2}$), ($T_{n-3}+T_{n-4}$), . . . (see FIG. 5). The software then proceeds to determine whether more than one independent complex rhythm is present based on values of the current variance (var), the current representative interval (rep), the previous variance ($var_{-1}$), and the previous representative interval ($rep_{-1}$).

At act 510, the software determines whether the current variance (var) is less than a threshold variance (THR) (e.g., 20 ms). If the current variance is not less than the threshold variance (THR), then the current chain of intervals is too statistically "random" to analyze and the software proceeds to act 345. If the current variance is less than the threshold variance (THR), then the current chain of intervals is statistically "stable" and the software proceeds to act 515.

At act 515, the software determines whether the previous variance (var) is less than a threshold variance (THR) (e.g., 20 ms). If the previous variance is not less than the threshold variance (THR), then the previous chain of intervals is too statistically "random" to analyze and the software proceeds to act 345. If the previous variance is less than the threshold variance (THR), then the previous chain of intervals is statistically "stable" and the software proceeds to act 520.

At act 520, the software determines whether the current interval ($T_n$) is shorter than half of the current representative interval (rep) (e.g., $T_n$<rep/2). If the current interval ($T_n$) is greater than or equal to half of the current representative interval (rep/2), then a cyclic artifact is not detected and the software proceeds to act 345). If the current interval ($T_n$) is less than half of the current representative interval (rep/2), then a cyclic artifact is possible and the software proceeds to act 525.

At act 525, the software determines whether the absolute magnitude of the difference between the current representative interval (rep) and the previous representative interval ($rep_{-1}$) is greater than a threshold value (THRV) (e.g., 10 ms). If the absolute magnitude of the difference between the current representative interval (rep) and the previous representative interval ($rep_{-1}$) is greater than a threshold value (THRV), then more than one cyclic artifact has been detected and the software proceeds to act 350. If the absolute magnitude of the difference between the current representative interval (rep) and the previous representative interval ($rep_{-1}$) is equal to or less than a threshold value (THRV), then more than one cyclic artifact has not been detected and the software proceeds to act 345.

At act 355, the DCA portion of the software provides the results of act 340 to another portion of the software for analysis. The software then selects the best leads for analysis as disclosed in U.S. patent application Ser. No. 09/421,683, entitled ELECTROCARDIOGRAM ARRANGEMENT. Of course, other methods for determining which lead to analyze can be used. For example, the first lead determined to contain only one independent cyclic rhythm may be selected for analysis.

At act 360, the software updates variables as necessary to prepare the software to analyze the next value (x) entering the DCA portion of the software. For example and as shown at act 605 in FIG. 9, refractory time (refract) is reduced by the rate (Ta), and the digital counter (tcnt) is increased by the rate (Ta). At act 610, a shift register storing the previous samples of value (x) is updated. The newest sample is in the most right element ($x_{-1}$) and the oldest in the most left element (e.g., $x_{-20\ ms}$). The shift register updates itself by shifting all the elements back in time (e.g., $x_{-20\ ms} = x_{-20\ ms+Ta}$, $x_{-2} = x_{-1}$, $x_{-1} = x$).

As can be seen from the above, the present invention provides for a method and apparatus for analyzing a physiological waveform and is particularly useful in detecting cyclic artifact in a physiological waveform. Various features and advantages of the invention are set forth in the following claims.

What is claimed is:

1. An exercise test device for acquiring and analyzing a multi-lead electrocardiogram (ECG) from a patient, the device comprising:
    input terminal for connection to a patient to acquire multi-lead ECG signals from the patient;
    instrumentation amplifier connected to the input terminal to filter the ECG signals and combine the signals to generate a multi-lead ECG;
    analysis module including a processor and software for operating the processor to detect cyclic artifact in the multi-lead ECG, wherein the cyclic artifact is detected by acquiring a trigger point in the multi-lead ECG, updating a shift register with a new trigger interval based on the trigger point, and determining whether two independent rhythms exist when a pre-determined number of trigger intervals have been recorded,
    and further wherein any of the leads may be selected for analysis based on a lack of cyclic artifact in that lead; and
    an analog-to-digital (A/D) converter connected between the instrumentation amplifier and the analysis module, wherein the multi-lead ECG generated by the instrumentation amplifier is an analog multi-lead ECG, wherein the A/D converter converts the analog multi-lead ECG to a digital mult-lead ECG and wherein the analysis module detects cyclic artifact in the digital multi-lead ECG.

2. An exercise test device as set forth in claim 1, the medical device further comprising:
    a display monitor connected to the analysis module, the display monitor capable of displaying the selected lead.

3. An exercise test device as set forth in claim 1, the medical device further comprising:
    a printer connected to the analysis module, the printer capable of printing the selected lead.

4. An exercise test device as set forth in claim 1, the medical device further comprising:
    an external storage device connected to the analysis module, the external storage device capable of storing the selected lead.

5. An exercise test device as set forth in claim 1, wherein the multi-lead ECG comprises twelve leads.

6. An exercise test device as set forth in claim 1, wherein the multi-lead ECG comprises seven leads.

7. An exercise test device for acquiring and analyzing a physiological waveform, the medical device comprising:
    an input terminal for connection to a patient to acquire the physiological waveform from a patient;
    an instrumentation amplifier connected to the input terminal to filter the physiological waveform;
    an analysis module including a processor and software for operating the processor to detect cyclic artifact in the physiological waveform, wherein the cyclic artifact is detected by acquiring a trigger point in the physiological waveform, updating a shift register with a new trigger interval based on the trigger point, and determining whether two independent rhythms exist when a pre-determined number of trigger intervals have been recorded; and
    an analog-to-digital (A/D) converter connected between the instrumentation amplifier and the analysis module, wherein the physiological waveform filtered by the instrumentation amplifier is an analog physiological waveform, wherein the A/D converter converts the analog physiological waveform to a digital physiological waveform.

8. An exercise test device as set forth in claim 7, the medical device further 10 comprising:
    a display monitor connected to the analysis module, the display monitor being capable of displaying the physiological waveform.

9. An exercise test device as set forth in claim 7, the medical device further comprising:
    a printer connected to the analysis module, the printer being capable of printing the physiological waveform.

10. An exercise test device as set forth in claim 7, the medical device further comprising:
    an external storage device connected to the analysis module, the external storage device being capable of storing the physiological waveform.

11. An exercise test device as set forth in claim 7, wherein the physiological waveform is a multi-lead ECG.

12. An exercise test device as set forth in claim 11, wherein the multi-lead ECG comprises twelve leads.

13. An exercise test device as set forth in claim 11, wherein the multi-lead ECG comprises five leads.

14. A medical device for acquiring and analyzing a physiological signal, the medical device comprising:
    an input terminal for connection to a patient to acquire a physiological signal from the patient;
    an instrumentation amplifier connected to the input terminal to filter and amplify the physiological signal resulting in a physiological waveform;
    means for detecting cyclic artifact in the physiological waveform, wherein the cyclic artifact is detected by acquiring a trigger point in the physiological waveform, updating a shift register with a new trigger interval based on the trigger point, and determining whether two independent rhythms exist when a pre-determined number of trigger intervals have been recorded; and
    an analog-to-digital (A/D) converter connected between the instrumentation amplifier and the means for detecting cyclic artifact,
    wherein the physiological waveform generated by the instrumentation amplifier is an analog physiological waveform to a digital physiological waveform and wherein the means for detecting cyclic artifact detects cyclic artifact in the physiological waveform.

15. A medical device as set forth in claim 14, the medical device further comprising:
    a display monitor connected to the means for detecting cyclic artifact, the display monitor being capable of displaying the physiological waveform.

16. A medical device as set forth in claim 14, the medical device further comprising:
    a printer connected to the means for detecting cyclic artifact, the printer being capable of printing the physiological waveform.

17. A medical device as set forth in claim 14, the medical device further comprising:
    an external storage device connected to the means for detecting cyclic artifact, the external storage device being capable of storing the physiological waveform.

18. A medical device as set forth in claim 14, wherein the means for detecting cyclic artifact comprises an analysis module having a processor and software for detecting cyclic artifact in the physiological waveform.

19. A medical device as set forth in claim 14, wherein the physiological signal is a multi-lead ECG signal, and wherein the physiological waveform is a multi-lead ECG.

20. A medical device as set forth in claim 19, wherein the multi-lead ECG comprises twelve leads.

21. A medical device as set forth in claim 19, wherein the multi-lead ECG comprises five leads.

22. A method of acquiring and analyzing a multi-lead electrocardiogram (ECG) from a patient, the method comprising:
    acquiring a set of multi-lead ECG signals from a patient;
    combining and filtering the set of multi-lead ECG signals to generate a multi-lead ECG;
    acquiring a trigger point in the multi-lead ECG;
    updating a shift register with a new trigger interval based on the trigger point;
    determining whether two independent rhythms exist when a pre-determined number of trigger intervals have been recorded, such that a second independent rhythm is the cyclic artifact; and
    selecting any of the leads that do not include two independent rhythms for analysis.

* * * * *